United States Patent [19]

Grollier

[11] Patent Number: 4,749,565

[45] Date of Patent: Jun. 7, 1988

[54] COSMETIC COMPOSITIONS BASED ON CATIONIC SILICONE, WATER-SOLUBLE HETEROPOLYSACCHARIDE AND ELECTROLYTE

[75] Inventor: Jean F. Grollier, Paris, France

[73] Assignee: L'Oreal, Paris, France

[21] Appl. No.: 775,019

[22] Filed: Sep. 11, 1985

[30] Foreign Application Priority Data

Sep. 21, 1984 [LU] Luxembourg ............................ 85549

[51] Int. Cl.$^4$ ........................ A45D 7/00; A61K 7/06; A61K 7/08
[52] U.S. Cl. ............................................ 424/70; 8/405; 8/406; 132/7; 424/62; 424/71; 424/72
[58] Field of Search ............................ 424/70; 536/123

[56] References Cited

U.S. PATENT DOCUMENTS

| | | | |
|---|---|---|---|
| 4,185,087 | 1/1980 | Morlino | 424/70 |
| 4,364,837 | 12/1982 | Pader | 424/70 |

FOREIGN PATENT DOCUMENTS

| | | | |
|---|---|---|---|
| 0017121 | 10/1980 | European Pat. Off. | 424/70 |
| 0023397 | 2/1981 | European Pat. Off. | 536/123 |
| 0064354 | 11/1982 | European Pat. Off. | 536/123 |
| 0095238 | 11/1983 | European Pat. Off. | 424/70 |
| 2058103 | 4/1981 | United Kingdom | 424/70 |
| 2058106 | 4/1981 | United Kingdom | 536/123 |
| 2058107 | 4/1981 | United Kingdom | 536/123 |
| 2098226 | 11/1982 | United Kingdom | 424/70 |
| 2136689 | 9/1984 | United Kingdom | 424/70 |

OTHER PUBLICATIONS

"Silicones for Ethnic Hair Care", Gant, Household and Personal Products Industry, vol. 20 (1983), Nov., No. 11, Ramseys, N.J., pp. 49, 52, 54, 57, 58.

"Information About Cosmetic Ingredients", Dow Corning, 1983.

*Primary Examiner*—Dale R. Ore
*Attorney, Agent, or Firm*—Cushman, Darby & Cushman

[57] ABSTRACT

Cosmetic composition based on cationic silicone, water-soluble heteropolysaccharide and electrolyte.

The invention relates to cosmetic compositions for the hair, containing, in a cosmetic medium suitable for application on the hair, at least one cationic silicone derivative which is a polysiloxane, one or more silicon atoms of which bear(s) an aminoaliphatic radical in which the amino groups are primary, secondary, tertiary or quaternary, at least one water-soluble heteropolysaccharide and at least one electrolyte.

13 Claims, No Drawings

COSMETIC COMPOSITIONS BASED ON CATIONIC SILICONE, WATER-SOLUBLE HETEROPOLYSACCHARIDE AND ELECTROLYTE

The present invention has as its subject new cosmetic compositions intended, in particular, for treating the hair, comprising at least one cationic silicone derivatives, at least one water-soluble heteropolysaccharide and at least an electrolyte.

Cationic silicone derivatives are well known in the field of hair-care cosmetics, and have been used as hair conditioning agents, investigated in particular for improving the disentangling of wet hair and endowing the hair with lustre and softness.

In the compositions in which they are used, they are generally present together with other cosmetic products for the purpose of endowing the hair with the desired cosmetic properties.

However, these compounds have the disadvantage of being sensitive to the addition of these products, and frequently give rise to compositions which separate very quickly into several phases.

The applicant has discovered that the addition of at least one water-soluble heteropolysaccharide and at least one electrolyte to the compositions containing cationic silicones made it easier to apply the composition on the hair, and further improved the softness and disentangling of wet hair. Furthermore, the dried hair is softer and less lank.

The applicant also observed, moreover, that by adding these products to compositions containing a cationic silicone derivative, it was, surprisingly, possible to overcome the problems of instability mentioned above.

The present invention has as its subject new cosmetic compositions intended, in particular, for the treatment and care of hair, comprising at least one cationic silicone derivative, a water-soluble heteropolysaccharide and an electrolyte.

Another subject of the invention consists of a process for treating the hair employing such compositions.

Other subjects will emerge on reading the description and examples which follow.

The compositions according to the invention are essentially characterised in that they contain, in a cosmetic medium suitable for application on the hair, at least one cationic silicone derivative which is a polysiloxane, one or more silicon atoms of which bear an aliphatic amino group in which the amine groups can be primary, secondary, tertiary or quaternary, at least one water-soluble heteropolysaccharide and at least one electrolyte.

The expression "aliphatic amino" encompasses alkylamino or hydroxyalkylamino radicals in which the alkyl chain can be interrupted by nitrogen or oxygen atoms.

The composition according to the invention preferably contains in addition a nonionic surfactant, and optionally a quaternary ammonium salt.

The cationic silicone derivatives more especially used in the compositions according to the invention are chosen from:

(a) the products of formula:

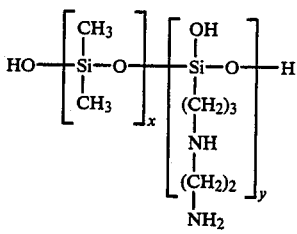

in which x and y are integers depending on the molecular weight, the average molecular weight being approximately between 5,000 and 10,000, sold under the name "amodimethicone" described, in particular, in the CTFA dictionary, 3rd edition 1982 (CFTA Cosmetic Dictionary, published by "The Cosmetic, Toiletry and Fragrance Association", Inc. 1133 Fifteenth Street NW Washington);

(b) cationic silicones corresponding to the general formula

in which $R_2$ is chosen from H, phenyl, OH, $C_1$–$C_8$ alkyl and preferably methyl; a can vary from 0 to 3, and preferably equals 0; b can vary from 0 to 1, and preferably equals 0; z+t can vary from 1 to 2,000, preferably from 50 to 150, with z varying from 0 to 1,999 and preferably from 49 to 149, and t varying from 1 to 2,000, preferably from 1 to 10; P is a monovalent radical of general formula:

$$C_nH_{2n}Z$$

in which n denotes an integer from 2 to 8 and Z is a group chosen from the following groups:

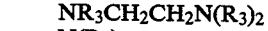
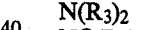
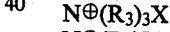
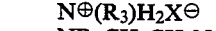

in which $R_3$ denotes hydrogen, phenyl, benzyl or a monovalent saturatedhydrocarbon radical containing from 1 to 20 carbon atoms, and X denotes a halogen atom;

(c) cationic silicone polymers corresponding to the formula

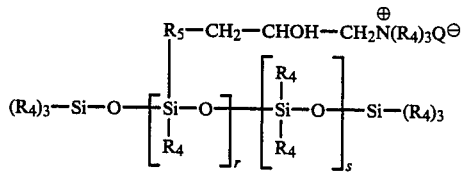

$R_4$ denotes a monovalent hydrocarbon radical having from 1 to 18 carbon atoms, especially an alkyl or alkenyl radical, and preferably methyl;

$R_5$ denotes a divalent hydrocarbon radical, preferably a $C_1$–$C_{18}$ alkylene radical or a divalent $C_1$–$C_{18}$, alkylene-oxy radical;

$Q^-$ is a halide ion (preferably chloride)

r denotes an average statistical value of 2 to 20, preferably from 2 to 8;

s denotes an average statistical value of 20 to 200, preferably from 20 to 50.

These compounds are described in greater detail in U.S. Pat. No. 4,185,087.

A very specially preferred polymer is that sold by UNION CARBIDE under the name "UCAR SILICONE ALE 56".

The composition can also contain surfactants. The surfactants are preferably chosen from nonionic surfactants, such as polyoxyethyleneated or polyglycerolated fatty alcohol derivatives or alkoxylphenol derivatives, polyoxyethyleneated fatty acid esters and condensates of ethylene oxide and propylene oxide, or from cationic surfactants such as quaternary ammonium salts, for example alkyldimethylbenzylammonium, alkyltrimethylammonium, alkyldimethylhydroxyethylammonium, dimethyldistearylammonium and dimethyldilaurylammonium chlorides or bromides, acetyldimethyldodecylammonium chloride, alkylamidoethyltrimethylammonium methosulphates, lactates of N,N-dimethylamino- (or N,N-diethylamino-) polyoxyethyl carboxylates containing 4 moles of ethylen oxide, alkylpyridinium salts such as 1-(2-hydroxyethyl)carbamoylmethylpyridinium chloride, N-(laurylcolaminoformylmethyl)pyridinium chloride, imidazoline derivatives such as alkylimidazolines, or mixtures thereof. The heteropolysaccharides used according to the invention are prepared by fermentation of suggars by microorganisms. They may comprise more particularly the xanthan gums produced by bacterium *Xanthomonas campestri* and the mutants or variants of this type of bacterium.

These gums have a viscosity of between 600 and 1,650 cP for an aqueous compositions containing 1% of xanthan gum, measured in a Brookfield type LVT viscometer at 60 rpm and have a molecular weight of between approximately 1,000,000 and 50,000,000. Xanthan gums comprise in their structure 3 different monosaccharides which are mannose, glucose and glucuronic acid as a salt.

Such products are, in particular, "KELTROL" marketed by KELCO, the 1% strength aqueous solutions of which have a Brookfield LVT viscosity at 60 rpm of 1,200 to 1,600 cP, KELZAN S marketed by KELCO, a 1% strength aqueous solution of which has a Brookfield LVT viscosity at 60 rpm of 850 cP, RHODOPOL 23, 23U and 23C marketed by RHONE-POULENC, a 0.3% strength aqueous solution of which as a Brookfield LVT viscosity at 30 rpm of 450+50 cP, RHODIGEL 23 sold by RHONE-POULENC, DEUTERON XG marketed by SCHONER GmbH, the viscosity of a 1% strength aqueous solution of which is 1,200 cP measured in a Brookfield LVT viscometer at 30 rpm, ACTIGUM CX 9 marketed by CECA having a viscosity of 1?200 cP measured in a Brookfield LVT viscometer at 30 rpm for a 1% strength aqueous solution, or the products sold by KELCO under the names KELZAN K3 B130, K8 B12 having a Haacke Rotovisco RVI, MVI viscosity at 25° C. of 1,000 cP at 10 s$^{-1}$ and K9 C57 the viscosity of a 1 strength aqueous solution of which is 630 to 1,000 cP measured in a Brookfield LVS viscometer at 60 rpm.

The heteropolysaccharides can also be selected from the group consisting of (a) a biopolymer PSD87 produced by the bacterium *Bacillus Polymyxa* the structure of which comprises glucose, galactose, mannose, fucose and glucuronic acid; this biopolymer PS87 is described in EP-A-23 397;

(b) biopolymer S88 produced by the strain Pseudomonas ATCC 31 554, the structure of which comprises rhamnose, glucose, mannose and glucuronic acid; this biopolymer is described in GB-A-2,058,106;

(c) biopolymer S130 produced by the strain Alcaligenes ATCC 31555, the molecule of which comprises rhamnose, glucose, mannose and glucuronic acid; this biopolymer is described in GB-A-2,058,107;

(d) biopolymer S 139 produced by the strain Pseudomonas ATCC 31644, the molecule of which comprises rhamnose, glucose, mannose, galactose and galacturonic acid; this biopolymer is described in U.S. Pat. No. 4,454,316;

(e) biopolymer S198 produced by the strain Alcalignes ATCC 31853, the molecule of which comprises rhamnose, glucose, mannose, and glucuronic acid; this biopolymer is described in EP-A-64 354;

(f) exocellular biopolymer produced by Gram-positive or -negative species of bacteria, yeasts, fungi or algae; this biopolymer is described biopolymer is described in DE-A No. 3,224,547.

The electrolyte which can be used in the cosmetic compositions according to the invention is chosen from alkali metal salts, such as sodium, potassium or lithium salts, these salts preferably being chosen from halides such as chloride and bromide, sulphates or salts of organic acids such as, in particular, acetates or lactates, as well as alkaline earth metal salts preferably chosen from calcium, magnesium and strontium carbonates, silicates, nitrates, acetates, gluconates, pantothenates and lactates.

An especially preferred cationic silicone derivatives is that sold under the tradename "Dow Corning 929 (DC 929)" cationic emulsion by DOW CHEMICAL COMPANY, which contains in combination (1) "amodimethycone", (2) "tallowtrimonium chloride" corresponding to the formula:

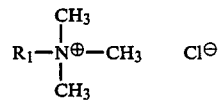

in which $R_1$ denotes a mixture of alkenyl and/or alkyl radicals having from 14 to 22 carbon atoms and derived form tallow fatty acids, and (3) "nonoxynol 10" corresponding to the formula:

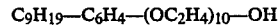

Another, more especially preferred cationic silicone derivative is that sold by DOW CORNING under the name "DOW CORNING O2 7224" which is a combination of:

(a) "trimethylsilylamodimethicone" corresponding to the formula:

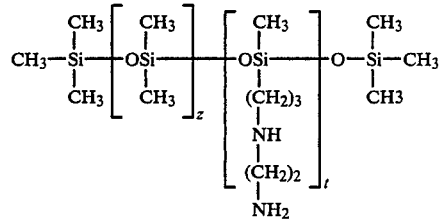

(b) "octoxynol-40" corresponding to the formula:

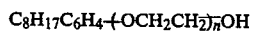

with n=40

(c) "isolaureth-6" of formula:

with n=6, and (d) glycol.

The cationic silicone derivative is present in the cosmetic compositions according to the invention in proportions of between approximately 0.1% and 5% by weight, and preferably from 0.5% to 2% by weight, relative to the total weight of the composition.

The water soluble heteropolysaccharide is present in the cosmetic compositions according to the invention to the extent of 0.1% to 2.5% by weight, and preferably between 0.2 and 1.5% by weight, relative to the total weight of the composition.

The electrolyte is present in the compositions according to the invention in proportions of between approximately 0.2% and 8% by weight, relative to the total weight of the composition.

The pH of the compositions is between 3 and 9, preferably between 4 and 6.

The cosmetic compositions according to the invention can contain, in addition to the cationic silicone derivative, the water-soluble heteropolysaccharide and the electrolyte, solvents and adjuvants customarily used in cosmetics, such as perfumes, colourings, preservatives, sequestering agents and any other adjuvants customarily used in compositions for the hair according to the application envisaged.

These compositions can, in particular, be used as shampoos, or products to be rinsed, for use before or after shampooing, colouring, bleaching, permanent waving or straightening.

When the compositions constitute shampoos, they contain in addition a surfactant.

These compositions are applied on the hair in sufficient proportions to impregnate in and, after a contact time of a few minutes, are removed by rinsing.

These compositions do not contain anionic polymers.

The examples which follow are intended to illustrate the invention without in any way being limitative in nature.

EXAMPLE 1

An after-shampoo having the following composition is prepared:

| | |
|---|---|
| Heteropolysaccharide sold under the name "Rhodopol 23 U" by RHONE-POULENC | 1.0 g |
| Sodium chloride | 4.0 g |
| Cationic silicone containing 35% AM sold under the name "DC 929" by DOW CORNING | 0.8 g-AM |
| Distearyldimethylammonium chloride | 0.3 g |
| pH adjusted to 7.1 by sodium hydroxide | |
| Water, colouring and preservatives qs | 100.0 g |

This composition is applied on washed and rinsed hair. After a few minutes' exposure, it is rinsed. An improvement is noted in the disentangling of the wet hair and the dry hair.

EXAMPLE 2

An after-shampoo having the following composition is prepared:

| | |
|---|---|
| Heteropolysaccharide sold under the name Keltrol by KELCO | 1.0 g |
| Cationic silicone sold at 35% AM under the name "Emulsion Q$_2$ 7224" by DOW CORNING | 1.75 g-AM |
| Sodium chloride | 4.0 g |
| pH adjusted to 7 with hydrochloric acid colouring, preservatives, perfume qs | |
| water qs | 100.0 g |

This composition is applied on washed and rinsed hair. After a few minutes' exposure, it is rinsed. The wet hair is disentangled more easily and is softer.

EXAMPLE 3

The following composition is prepared:

| | |
|---|---|
| Heteropolysaccharide sold under the name Keltrol by KELCO | 2.0 g |
| Sodium chloride | 4.0 g |
| Cationic silicone sold at 35% AM under the name UCAR silicone ALE 56 by UNION CARBIDE | 1.0 g-AM |
| Copolymer of dimethyldiallylammonium chloride and acrylamide of MW 500,000 sold at 8% AM under the name Merquat 550 by MERCK | 0.3 g-AM |
| Colourings, preservatives, perfume qs | |
| pH adjusted to 7 with sodium hydroxide | |
| Water qs | 100.0 g |

This composition is applied after shampooing on wet, wrung hair. It is left in place for a few moments. The hair is then rinsed. This composition contributes softness and manageability.

EXAMPLE 4

An after-shampoo of the following composition is prepared:

| | |
|---|---|
| heteropolysaccharide sold under the name Kelzan K8 B12 by KELCO | 1.2 g |
| Cationic silicone sold at 35% AM under the name UCAR silicone ALE 56 by UNION CARBIDE | 0.6 g-AM |
| Sodium chloride | 0.2 g |
| Colouring, preservatives, perfume qs | |
| pH adjusted to 6 with hydrochloric acid | |
| Water qs | 100.0 g |

EXAMPLE 5

A shampoo having the following composition is prepared:

| | |
|---|---|
| (C$_{12}$-C$_{18}$) alkyldimethylcarboxymethyl ammonium hydroxide sold at 30% AM under the name Dehyton AB30 by HENKEL | 8.0 g-AM |
| Sodium alkyl(C$_{12}$-C$_{14}$) ether sulphate containing 2.2 moles of ethylene oxide | 4.0 g-AM |
| Heteropolysaccharide sold under the name Kelzan K3 B130 by KELCO | 0.7 g |
| Cationic silicone sold at 35% AM under the name Cationic Emulsion DC 929 by DOW CORNING | 0.4 g-AM |
| Sodium chloride | 0.5 g |

| -continued | |
|---|---|
| Colourings, preservatives, perfume | qs |
| pH adjusted to 5.5 with sodium hydroxide | |
| Water qs | 100.0 g. |

I claim:

1. A stable cosmetic composition for application to the hair so as to improve the softness and disentanglement of wet hair and to improve the softness of dry hair, said composition comprising in an aqueous cosmetic medium suitable for application to the hair
   (i) at least one cationic silicone derivative which is a polysiloxane having one or more silicon atoms carrying an aminoaliphatic radical in which the amino groups are primary, secondary, tertiary or quaternary,
   (ii) at least one water-soluble heteropolysaccharide selected from the group consisting of
      (a) a xanthum gum having a molecular weight ranging between about 1,000,000 and 50,000,000,
      (b) bipolymer PS87 produced by bacterium *Bacillus Polymyxa*, the structure of which comprises glucose, galactose, mannose, fucose and glucuronic acid,
      (c) bipolymer S88 produced by the strain Pseudomonas ATCC 31554, the molecule of which comprises rhamnose, glucose, mannose and glucuronic acid,
      (d) bipolymer S130 produced by the strain Alcaligenes ATCC 3155, the molecule of which comprises rhamnose, glucose, mannose and glucuronic acid,
      (e) bipolymer S198 produced by the strain Alcaligenes ATCC 31853, the molecule of which comprises rhamnose, glucose, mannose and glucuronic acid,
      (f) bipolymer S139 produced by the strain Pseudomonas ATCC 31644, the molecule of which comprises rhamnose, glucose, mannose, galactose and galacturonic acid, and
      (g) exocellular bipolymer produced by gram positive or negative species of bacteria, yeasts, fungi and algae, and
   (iii) at least one electrolyte selected from an alkali metal salt or alkaline earth metal salt,
   said cationic silicone derivative being present in an amount ranging from 0.1 to 5 weight percent based on the total weight of the composition,
   said water-soluble heteropolysaccharide being present in an amount ranging from 0.1 to 2.5 weight percent based on the total weight of the composition, and
   said electrolyte being present in an amount ranging from 0.2 to 8 weight percent based on the total weight of said compositon.

2. The composition of claim 1 wherein said cationic silicone derivative is selected from the group consisting of
   (a) a compound having the formula:

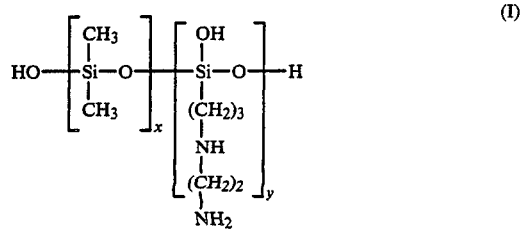

(I)

wherein
x and y are integers ranging from about 5,000 to 10,000, (b) a compound having the formula

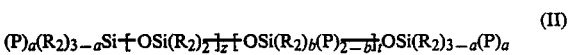

(II)

wherein
$R_2$ is selected from the group consisting of hydrogen, phenyl, OH and alkyl having 1–8 carbon atoms,
a ranges from 0 to 3,
b ranges from 0 to 1,
z+t ranges from 1 to 2,000,
z ranges from 9 to 1,999,
t ranges from 1 to 2,000,
P is a monovalent radical having the formula:

$C_nH_{2n}Z$ wherein
n is an integer ranging from 2 to 8 and
Z represents a member selected from the group consisting of
   (1) $-NR_3CH_2CH_2N(R_3)_2$,
   (2) $-N(R_3)_2$,
   (3) $N^{\oplus}(R_3)_3X^{\ominus}$,
   (4) $N^{\oplus}(R_3)H_2X^{\ominus}$ and
   (50 $NR_3CH_2CH_2N^{\oplus}(R_3)H_2X^{\ominus}$
wherein
$R_3$ represents hydrogen, phenyl, benzyl or a monovalent saturated hydrocarbon radical containing from 1 to 20 carbon atoms, and
X represents a halogen atom, and (c) a compound having the formula:

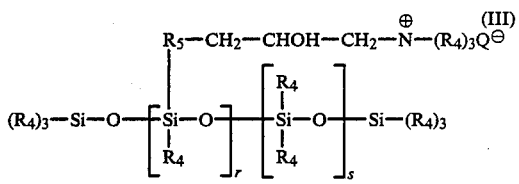

(III)

wherein
$R_4$ represents a monovalent hydrocarbon radical having 1 to 18 carbon atoms,
$R_5$ represents a divalent alkylene radical having 1–18 carbon atoms or a divalent alkylene-oxy radical wherein the alkylene moiety has 1–18 carbon atoms,
$Q^{\ominus}$ is a halide ion,
r represents an average statistical value ranging from 2 to 20 and s represents an average statistical value ranging from 20 to 200.

3. The composition of claim 1 which also contains a surfactant.

4. The composition of claim 3 wherein said surfactant is a nonionic surfactant selected from the group consisting of
(i) polyoxyethylenated fatty alcohol,
(ii) polyoxyethylenated alkyl phenol,
(iii) polyglycerolated fatty alcohol,
(iv) polyglycerolated alkyl phenol,
(v) polyoxyethylenated fatty acid ester and
(vi) a condensate of ethylene oxide and propylene oxide.

5. The composition of claim 3 wherein said surfactant is a cationic surfactant, said cationic surfactant being a quaternary ammonium salt.

6. The composition of claim 1 comprising a mixture of
(a) said compound of formula I,
(b) a compound having the formula

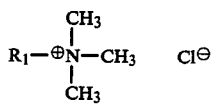

wherein
$R_1$ represents (i) a mixture of alkenyl radicals having 14 to 22 carbon atoms, (ii) a mixture of alkyl radicals having 14 to 22 carbon atoms or (iii) a mixture of alkenyl and alkyl radicals, having 14 to 22 carbon atoms, and derived from tallow fatty acids, and
(c) a compound having the formula:

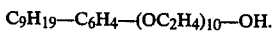

7. The composition of claim 1 comprising a mixture of
(a) a compound having the formula

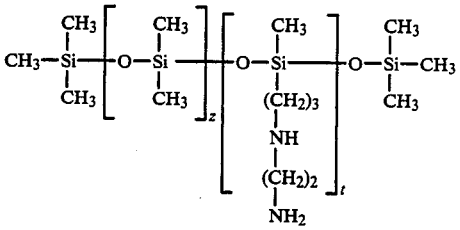

(b) a compound having the formula

wherein n is 40,
(c) a compound having the formula

wherein n is 6, and
(d) glycol.

8. The composition of claim 1 wherein said alkali metal salt is selected from the group consisting of alkali metal halide, alkali metal sulfate and alkali metal salt of an organic acid.

9. The composition of claim 1 wherein said xanthan gum has a viscosity ranging from 600 to 1,650 cP for an aqueous composition containing 1 percent of xanthan gum, measured in a Brookfield type LVT viscometer at 60 rpm.

10. The composition of claim 1 having a pH ranging from 3 to 9.

11. The composition of claim 1 which also includes one or more of a perfume, a coloring agent, a preservative and a sequestering agent.

12. A process for treating the hair comprising applying to the hair a sufficient amount of the composition of claim 1 so as to impregnate the hair, permitting said composition to remain in contact with the hair for a time sufficient to treat the hair and thereafter rinsing the hair.

13. The process of claim 12 wherein said composition is in the form of a shampoo and contains a surfactant.

* * * * *

UNITED STATES PATENT AND TRADEMARK OFFICE
CERTIFICATE OF CORRECTION

PATENT NO. : 4,749,565
DATED : June 7, 1988
INVENTOR(S) : Jean F. Grollier

It is certified that error appears in the above-identified patent and that said Letters Patent is hereby corrected as shown below:

Col. 7, each of lines 24, 28, 32, 36, 40, 44,

"bipolymer" should read --biopolymer--.

Signed and Sealed this

Thirty-first Day of January, 1989

Attest:

DONALD J. QUIGG

Attesting Officer

Commissioner of Patents and Trademarks